United States Patent [19]

Jakubowski et al.

[11] Patent Number: 5,550,118
[45] Date of Patent: Aug. 27, 1996

[54] POLYHYDRONORHARMAN SYNTHASE INHIBITORS

[75] Inventors: Joseph A. Jakubowski, Indianapolis; Alan D. Palkowitz, Carmel; Sandra K. Sigmund, Indianapolis, all of Ind.

[73] Assignee: Eli Lilly and Company, Indianapolis, Ind.

[21] Appl. No.: 189,213

[22] Filed: Jan. 31, 1994

[51] Int. Cl.⁶ .................. A61K 31/44; A61K 31/675; C07F 9/58; C07D 471/04
[52] U.S. Cl. ............... 514/89; 514/292; 546/85; 546/86; 546/87
[58] Field of Search .................. 546/85, 86, 87, 546/23; 514/292, 89

[56] References Cited

U.S. PATENT DOCUMENTS

| | | | |
|---|---|---|---|
| 2,850,501 | 9/1958 | Voegtli | 546/85 |
| 4,855,295 | 8/1989 | Biere et al. | 514/232.8 |
| 5,066,649 | 11/1991 | Hamminga et al. | 514/183 |
| 5,328,905 | 7/1994 | Hamminga et al. | 514/214 |

*Primary Examiner*—Alan L. Rotman
*Attorney, Agent, or Firm*—Roger S. Benjamin; David E. Boone

[57] ABSTRACT

Selected acid functional polyhydronorharman type derivatives effective as thromboxane synthase inhibitors having the formula:

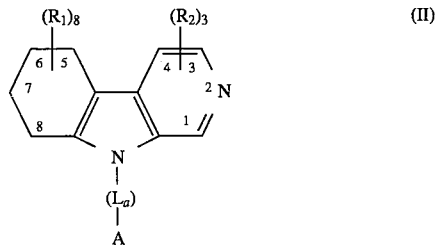

where $R_1$ and $R_2$ are monovalent radicals, $-(L_a)-$ is a linking group of 4 to 8 chain atoms, and A is an acidic group.

7 Claims, No Drawings

POLYHYDRONORHARMAN SYNTHASE INHIBITORS

FIELD OF THE INVENTION

This invention concerns norharman compounds useful as thromboxane synthase inhibitors.

BACKGROUND OF THE INVENTION

The tricyclic compound, norharman (CA Registry No. 244-63-3), is also known as beta-carboline; carbazoline; 2-azacarbazole; 2,9-diazafluorene; and 9H-pyrido (3,4-β) indole.

The preparation of certain esters of 9-pyrido(3,4-β)indole alkanoic acids is described in U.S. Pat. No. 2,850,501.

U.S. Pat. No. 5,066,649 describes various 8,9-annelated 1,2,3,4-tetrahydro-beta-carbolines as orally active fibrinolytics.

Therapeutic agents for specifically reducing the production of thromboxane $A_2$ are useful for treatment of conditions such as renal disease, (e.g., hydronephrosis, transplant rejection, and renal nephritis) pulmonary disease, (e.g., asthma, and pulmonary hypertension), prevention and treatment of hepatic and intestinal damage, cardiovascular diseases (e.g., arteriosclerosis, thrombosis, hypertension, and shock) or resulting from surgical procedures such as angioplasty and coronary bypass surgery. Aspirin has utility as a nonspecific indirect inhibitor of thromboxane synthesis; however, it is desirable to discover new compounds having more potent and specific TSI properties than aspirin.

SUMMARY OF THE INVENTION

This invention is a novel series of polyhydronorharman type compounds which inactivate $TXA_2$ synthase in human blood platelets and other cells, said compounds having the general structural formula (I):

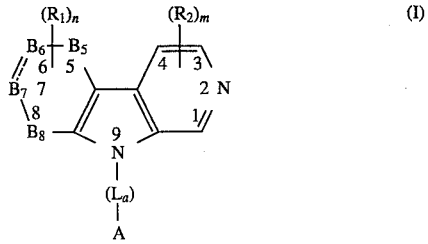

This invention is also a pharmaceutical formulation containing as active ingredient the polyhydronorharman compounds of formula (I); where $R_1$, $R_2$, n, m, $L_a$, A, $B_5$, $B_6$, $B_7$ and $B_8$ are as hereinafter defined.

This invention is also a multi-component pharmaceutical composition comprising the polyhydronorharman compound of the invention together with thrombolytic agents, angiotensin converting enzyme inhibitors, and/or thromboxane receptor antagonists.

This invention is a method of inhibiting thromboxane production by giving a mammal a therapeutically effective dose of a compound of the invention.

This invention is also an improved method of conducting surgical operations such as angioplasty and bypass surgery by administration to the patient a therapeutically effective dose of a compound of the invention.

DETAILED DESCRIPTION OF THE INVENTION

This invention relates to new thromboxane synthase inhibitors, and their use as antithrombotic agents for prophylaxis and treatment of thromboembolic diseases such as venous thrombosis, pulmonary embolism, arterial thrombosis, in particular myocardial ischemia, myocardial infarction and cerebral thrombosis, general hypercoagulable states and local hypercoagulable states such as following angioplasty and coronary bypass operations, and generalized tissue injury as it relates to the inflammatory process.

The following terms, have the definitions set out below:

The term "halo means a radical derived from fluorine, chlorine, bromine, or iodine.

The term "alkyl" by itself or as part of another substituent, unless otherwise stated means a straight or branched chain alkyl radical having the stated number of carbon atoms such as methyl, ethyl, n-propyl, isopropyl, n-butyl, and tertiary-butyl.

The term "aryl" as used herein refers to an organic radical derived from an aromatic hydrocarbon by removal of one atom; e.g., phenyl, and naphthyl.

The term "substituted phenyl" means a phenyl radical substituted at one or more positions by one or more acyl, $C_1$–$C_6$ alkyl, $C_2$–$C_6$ alkenyl, $C_2$–$C_6$ alkynyl, $C_1$–$C_6$ alkoxy, halo, nitro, sulfo, amino, or hydroxyl groups.

The term "acidic group" refers to an organic radical which is a proton donor.

The term "effective amount" as used herein, means an amount of the compound of the invention which is capable of inactivating $TXA_2$ synthase in human blood platelets and other cells to an extent which achieves a beneficial therapeutic and/or prophylactic result.

The words "pharmacologically acceptable salts" include both acid and base addition salts.

The words "chain atoms" means the number of atoms in the shortest chain between the two bonds of the linking group —($L_a$)—. The presence of a benzene or cyclohexane ring in the shortest chain counts as two atoms. For example, the linking groups (a) and (b);

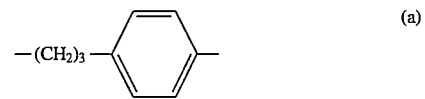

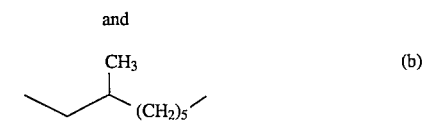

have 5 and 7 chain atoms, respectively.

I. Compounds of the Invention

The novel compounds of the invention are represented by Formula (I) or a pharmacologically acceptable salt or prodrug thereof:

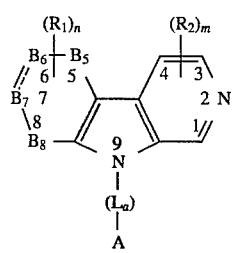

The dashed line in formula (I) above indicates optional unsaturation, namely, of one or no double bonds in the ring having the $B_5$, $B_6$, $B_7$ and $B_8$ atoms. Formula (I) represents any of structures Ia thru Id below. The unsaturation, in the case of one optional double bond being present results in structures Ia thru Ic depicted below. No optional double bond results in structure Id, below.

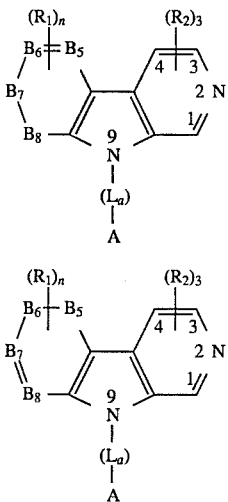

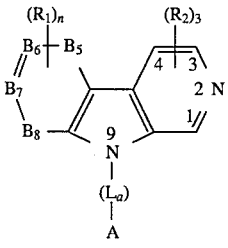

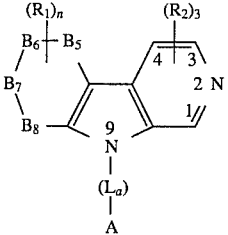

and wherein;

n is an integer from 4 to 8;

$B_5$, $B_6$, $B_7$, and $B_8$ are selected from the group consisting of carbon, nitrogen, oxygen, and sulfur with the proviso that at least two of $B_5$, $B_6$, $B_7$, or $B_8$ are carbon;

$R_1$ is a radical at position 5, 6, 7, and 8 where each $R_1$ is independently selected from hydrogen, hydroxy, halo, cyano, sulfo, nitro, amino, substituted amino, carboxyl, acyl, carbamyl, carbonyl, alkoxycarbonyl, aryl, aryloxy, $C_1$–$C_{12}$ alkyl, $C_2$–$C_{12}$ alkenyl, $C_2$–$C_{12}$ alkynyl, $C_1$–$C_{12}$ alkoxy, $C_4$–$C_8$ cycloalkyl, $C_1$–$C_{12}$ halogenated alkyl, $C_1$–$C_{12}$ hydroxylated alkyl, $C_1$–$C_{12}$ substituted phenyl, the phenyl of which may optionally be substituted by alkyl, halo, hydroxy, $C_1$–$C_6$ alkenyl, $C_1$–$C_6$ alkynyl, $C_1$–$C_6$ alkylthio, acyl, $C_1$–$C_6$ alkoxy, or $C_1$–$C_6$ alkylsulfonyl;

$R_2$ is a radical at position 1, 3 or 4 where each $R_2$ is independently selected from hydrogen, hydroxy, halo, cyano, sulfo, nitro, amino, substituted amino, carboxyl, acyl, carbamyl, carbonyl, alkoxycarbonyl, aryl, aryloxy, $C_1$–$C_{12}$ alkyl, $C_2$–$C_{12}$ alkenyl, $C_2$–$C_{12}$ alkynyl, $C_1$–$C_{12}$ alkoxy, $C_4$–$C_8$ cycloalkyl, $C_1$–$C_{12}$ halogenated alkyl, $C_1$–$C_{12}$ hydroxylated alkyl, $C_1$–$C_{12}$ substituted phenyl, the phenyl of which may optionally be substituted by alkyl, halo, hydroxy, $C_1$–$C_6$ alkenyl, $C_1$–$C_6$ alkynyl, $C_1$–$C_6$ alkylthio, acyl, $C_1$–$C_6$ alkoxy, or $C_1$–$C_6$ alkylsulfonyl;

$(L_a)$ is a divalent linking group; and

A is an acidic group.

Preferred compounds of the invention are those wherein each $R_1$ is hydrogen and/or each $R_2$ is hydrogen.

Preferred are compounds of formula (I) wherein the acidic group A is selected from the following:

—5-tetrazolyl,

—$SO_3H$

—carboxyl

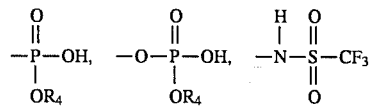

and where $R_4$ is selected from hydrogen, $C_1$–$C_{12}$ alkyl, phenyl or substituted phenyl.

Most preferred are compounds of formula (I) wherein the acidic group is carboxyl.

Also preferred are compounds of formula (I) wherein the divalent linking group —$(L_a)$— has from 4 to 8 chain atoms and most preferably 5 or 6 chain atoms. Particularly preferred are compounds of Formula (I) wherein the divalent linking group, —$(L_a)$—, is selected from the following formulae:

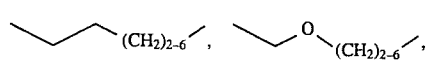

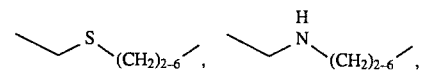

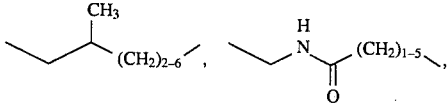

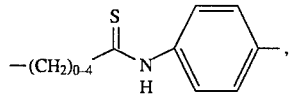

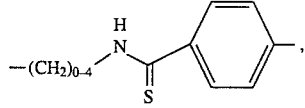

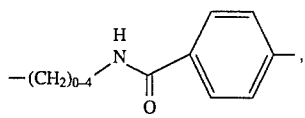

A preferred subset of Formula (I) polyhydronorharman compounds which inactivate TXA$_2$ synthase in human blood platelets and other cells is represented by Formula (II) and pharmacologically acceptable salts, solvates, or prodrugs thereof;

$$\text{(II)}$$

wherein;

R$_1$ is a radical at position 5, 6, 7, and 8 where each R$_1$ is independently selected from hydrogen, hydroxy, halo, cyano, sulfo, nitro, amino, substituted amino, carboxyl, acyl, carbamyl, carbonyl, alkoxycarbonyl, aryl, aryloxy, C$_1$–C$_{12}$ alkyl, C$_2$–C$_{12}$ alkenyl, C$_2$–C$_{12}$ alkynyl, C$_1$–C$_{12}$ alkoxy, C$_4$–C$_8$ cycloalkyl, C$_1$–C$_{12}$ halogenated alkyl, C$_1$–C$_{12}$ hydroxylated alkyl, C$_1$–C$_{12}$ substituted phenyl, the phenyl of which may optionally be substituted by alkyl, halo, hydroxy, C$_1$–C$_6$ alkenyl, C$_1$–C$_6$ alkynyl, C$_1$–C$_6$ alkylthio, acyl, C$_1$–C$_6$ alkoxy, or C$_1$–C$_6$ alkylsulfonyl;

R$_2$ is a radical at position 1, 3 or 4 where each R$_2$ is independently selected from hydrogen, hydroxy, halo, cyano, sulfo, nitro, amino, substituted amino, carboxyl, acyl, carbamyl, carbonyl, alkoxycarbonyl, aryl, aryloxy, C$_1$–C$_{12}$ alkyl, C$_2$–C$_{12}$ alkenyl, C$_2$–C$_{12}$ alkynyl, C$_1$–C$_{12}$ alkoxy, C$_4$–C$_8$ cycloalkyl, C$_1$–C$_{12}$ halogenated alkyl, C$_1$–C$_{12}$ hydroxylated alkyl, C$_1$–C$_{12}$ substituted phenyl, the phenyl of which may optionally be substituted by alkyl, halo, hydroxy, C$_1$–C$_6$ alkenyl, C$_1$–C$_6$ alkynyl, C$_1$–C$_6$ alkylthio, acyl, C$_1$–C$_6$ alkoxy, or C$_1$–C$_6$ alkylsulfonyl;

(L$_a$) is a divalent linking group containing from 4 to 6 chain atoms; and

A is an acidic group.

Preferred compounds of formula (II) are those wherein each R$_1$ is hydrogen and/or each R$_2$ is hydrogen, and A is carboxyl.

A preferred subset of Formula (II) polyhydronorharman compounds which inactivate TXA$_2$ synthase in human blood platelets and other cells is represented by Formula (III) and pharmacologically acceptable salts or prodrugs thereof.

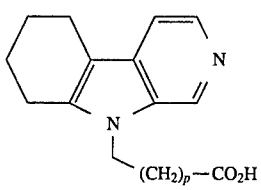

wherein;

p is an integer 4 or 5.

Specific preferred compounds and all pharmaceutically acceptable salts, solvates and prodrug derivatives thereof which are illustrative of the compounds of the invention include the following:

(a) ethyl 5,6,7,8-tetrahydro-β-carboline-1-pentanoate,
(b) ethyl 5,6,7,8-tetrahydro-β-carboline-1-hexanoate,
(c) ethyl 5,6,7,8-tetrahydro-β-carboline-1-heptanoate, and
(d) mixtures of any of (a) thru (c)

The compounds of the invention possess at least one acidic functional substituent (viz., group A of Formula I) and, as such, are capable of forming salts. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion exchange resin.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1–19 (1977)).

In those instances where the compounds of the invention contain a basic group(s) they may be reacted with suitable organic or inorganic acids to form salts such as acetate, benzenesulfonate, benzoate, bicarbonate, bisulfate, bitartrate, borate, bromide, camsylate, carbonate, chloride, clavulanate, citrate, chloride, edetate, edisylate, estolate, esylate, fluoride, fumarate, gluceptate, gluconate, glutamate, glycolylarsanilate, hexylresorcinate, bromide, chloride, hydroxynaphthoate, iodide, isothionate, lactate, lactobionate, laurate, malate, malseate, mandelate, mesylate, methylbromide, methylnitrate, methylsulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate.

The compounds of the formula (I) can also be in the form of zwitterions, since they contain both acidic and basic functionality and are capable of self-protonation.

Certain compounds of the invention possess one or more chiral centers and may thus exist in optically active forms. Likewise, when the compounds contain an alkenyl or alkenylene group there exists the possibility of cis- and trans-isomeric forms of the compounds. The R- and S- isomers and mixtures thereof, including racemic mixtures as well as mixtures of cis- and trans- isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods.

Prodrugs are derivatives of the compounds of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., Design of Prodrugs, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy) alkyl esters or ((alkoxycarbonyl)oxy)alkyl esters.

II. Pharmaceutical Formulations of the Invention

This invention also provides pharmaceutical formulations comprising a novel compound as described in the preceding Section I or a pharmaceutically acceptable salt or prodrug thereof.

For the pharmaceutical formulations any suitable carrier known in the art can be used. In such a formulation, the carrier may be a solid, liquid, or mixture of a solid and a liquid. Solid form formulations include powders, tablets and capsules. A solid carrier can be one or more substances which may also act as flavoring agents, lubricants, solubilisers, suspending agents, binders, tablet disintegrating agents and encapsulating material.

In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from about 1 to about 99 weight percent of the active ingredient which is the novel compound of this invention. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs.

The active ingredient can be dissolved or suspended in a pharmaceutically acceptable carrier, such as sterile water, sterile organic solvent or a mixture of both. The active ingredient can often be dissolved in a suitable organic solvent, for instance aqueous propylene glycol. Other compositions can be made by dispersing the finely divided active ingredient in aqueous starch or sodium carboxymethyl cellulose solution or in a suitable oil.

Preferably the pharmaceutical formulation is in unit dosage form. The unit dosage form can be a capsule or tablet itself, or the appropriate number of any of these. The quantity of active ingredient in a unit dose of composition may be varied or adjusted from about 0.1 to about 1000 milligrams or more according to the particular treatment involved. It may be appreciated that it may be necessary to make routine variations to the dosage depending on the age and condition of the patient. The dosage will also depend on the route of administration.

The formulations according to the invention may be made for oral, parenteral or rectal administration or in a form suitable for administration by inhalation or insufflation, either through the mouth or nose.

The following pharmaceutical formulations 1 thru 8 are illustrative only and are not intended to limit the scope of the invention in any way. "Active ingredient," refers to a compound according to Formula (I) or a pharmaceutically acceptable salt, solvate, or prodrug thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

|  | Quantity (mg/tablet) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

Formulation 3

An aerosol solution is prepared containing the following components:

|  | Weight |
| --- | --- |
| Active ingredient | 0.25 |
| Ethanol | 25.75 |
| Propellant 22 (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| Active ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| Active ingredient | 80 mg |
| --- | --- |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| Active ingredient | 225 mg |
| --- | --- |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| Active ingredient | 50 mg |
| --- | --- |
| Sodium carboxymethyl cellulose | 50 mg |
| Syrup | 1.25 ml |

| | |
|---|---|
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| | |
|---|---|
| Active ingredient | 100 mg |
| Isotonic saline | 1,000 ml |

The solution of the above ingredients generally is administered intravenously to a subject at a rate of 1 ml per minute. The pharmaceutical formulations of the invention inactivate $TXA_2$ synthase in human blood platelets and other cells.

III. Multi-Mode Pharmaceutical Formulations Using Compounds of the Invention in combination with Selected Therapeutic Agents The compounds of the invention act as thromboxane synthase inhibitors and are advantageously combined with other agents having different modes of action to give multi-mode pharmaceutical compositions. The resultant combination of ingredients may be used as Active Ingredient in the pharmaceutical formulations described in Section II, above. Thus, an Active Ingredient (for multi-mode pharmaceutical formulations) may be formed by combining the compounds of this invention (as represented by Formulae I, II, and III) with therapeutic agents selected from one or more of the following classes:

a) thrombolytic agents;

b) angiotensin converting enzyme inhibitors;

c) thromboxane receptor antagonists.

Examples of thrombolytic agents (a) are tissue plasminogen activator (t-PA) and streptokinase. These agents would be preferably used in combination with the compounds of the invention for cardiovascular indications.

Angiotensin converting enzyme inhibitors (b) (ACE inhibitors) such as captopril, (1-[(2S)-3-mercapto-2-methylpropionyl]-L-proline would be preferably used in combination with the compounds of the invention for renal indications such as diabetic nephropathy.

Examples of thromboxane receptor antagonists (c) are Vapiprost (Glaxo) and S-1452™ compound (CAS Reg. No.132747-47- 8); (5-Heptanoic acid, 7-[3-[(phenylsulfonyl)amino]bicyclo[2.2.1]hept-2-yl]-calcium salt (2:1), [1R-[1α,2α(Z),3β,4β]]; and VAPIPROST™ compound (CAS Reg. No. 87248- 13-3); [1R-[1α(Z), 2β,3β5α]]-(+)-7-[5-[(1, 1'-Biphenyl)- 4-ylmethoxy]- 3-hydroxy-2-(1-piperidinyl)cyclopentyl]-4-heptenoic acid hydrochloride; and Bay-u-3405™ compound (CAS Reg. No.116649-85-5); (9H-Carbazole-9-propanoic acid, 3-[[(4-fluorophenyl)sulfonyl]amino]-1,2,3,4-tetrahydro, (R)-. These antagonists would preferably be used in combination with the compounds of the invention for cardiovascular and renal indications. Combinations of the compounds of the invention with thromboxane receptor antagonist (TRA) is a preferred aspect of this invention, because the (TRA) blocks the activity of prostaglandin $H_2$ which is enhanced by the thromboxane synthase inhibitor compounds of the invention (represented by formulae I, II, and III).

The relative proportions of ingredients (weight ratio of compounds of the invention to therapeutic agent) will generally be in the range of from 1 to 1000 to 1000 to 1 and is readily determined by combining dosages of the ingredients in weights known to be pharmaceutically effective.

Multi-mode pharmaceutical composition may be formed by admixing the compounds of the invention with one or more classes of therapeutic agent (a), (b), or (c) listed above. Alternatively, each ingredient, (i) the compound of the invention, and (ii) the selected therapeutic agent may be packaged together, for example in a tablet having two parts, so their administration to the patient is concurrent.

IV. An Improved Method of Inhibiting Thromboxane Production Using Compounds of the Invention This invention is a method for inhibiting thromboxane production which comprises administering to a mammalian host (e.g. human) an effective amount of the novel compounds for formulae (I), (II), or (III). The treatment of a mammal with the compounds of the invention may be for either therapeutic and/or prophylactic purposes.

A preferred method of the invention for inhibiting thromboxane production is administration to a mammal of the pharmaceutical formulations of the invention described in Section II, above, or the multi-mode pharmaceutical formulations described in Section III, above.

A specific dose of a compound of the invention administered to obtain therapeutic and/or prophylactic effects will, of course, be determined by the particular circumstances surrounding the case, including, for example, the route of administration and the condition being treated. A typical daily dose will contain a non-toxic dosage level of compound of from about 0.01 mg/kg to about 50 mg/kg of body weight. Preferred daily doses generally will be from about 0.05 mg/kg to about 20 mg/kg.

This invention is also an improved method of conducting angioplasty by administering before and/or during the angioplasty the thrombosis preventing novel compounds of formulae (I), (II) or (III).

This invention is a method for the prevention or treatment of a first or recurrent myocardial infarction or a first or recurrent stroke in a human comprising administering to the human in an amount effective for prevention or treatment of a first or recurrent myocardial infarction for first or recurrent stroke, a combination of active ingredients comprising the compounds of formulae (I), (II) or (III) or a pharmaceutically acceptable salt or prodrug thereof.

V. Method of Preparing the Beta-Carboline Compounds of the Invention

Scheme 1 is an illustrative reaction sequence for preparation of 5,6,7,8-tetrahydro-β-carboline-1-alkanoic acids.

Scheme 1

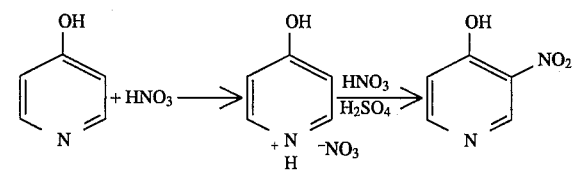

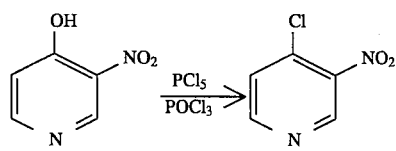

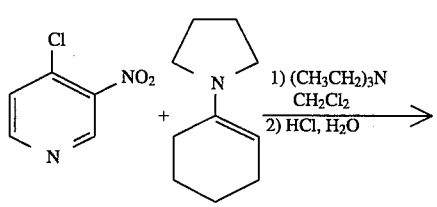

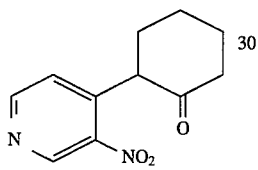

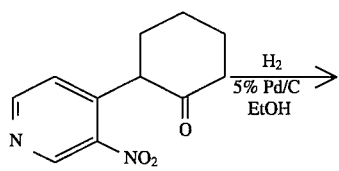

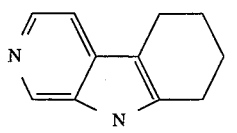

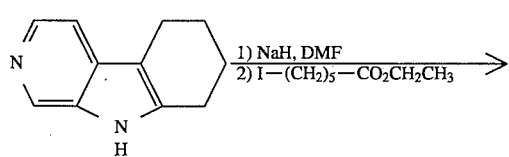

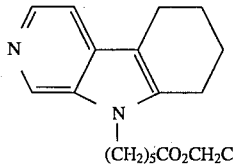

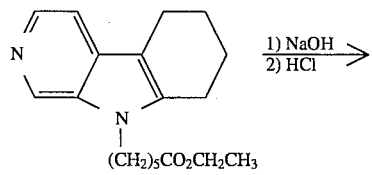

-continued
Scheme 1

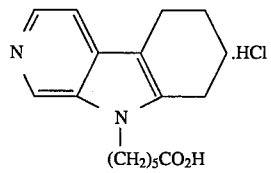

Fuming nitric and sulfuric acids are employed to nitrate 4-hydroxypyridine to produce 4-hydroxy-3-nitropyridine. The 4-hydroxy-3-nitropyridine is converted to 4-chloro-3-nitropyridine by heating with $PC_{15}$ and $POCl_3$. Reacting 4-chloro-3-nitropyridine with 1-(1-pyrrolidino)cyclohexene in $CH_2C_{12}$ with added triethylamine produces 2-(2-nitro-4-pyridyl)cyclohexanone which, upon hydrogenation, provides 5,6,7,8-tetrahydro-β-carboline. Deprotonation of the 5,6,7,8-tetrahydro-β-carboline with base and subsequent alkylation with a suitable alkyl ω-halo-alkanoate gives alkyl 5,6,7,8-tetrahydro-β-carboline-1alkanoate which may then be hydrolyzed with base to provide the corresponding 5,6,7,8-tetrahydro-β-carboline-1-alkanoic acid.

The following Examples are intended to illustrate the invention and are not to be construed as being limitations thereon. Temperatures are given in degrees Centigrade and all parts wherever given are parts by weight unless otherwise indicated.

EXAMPLES

Example 1

Part A:

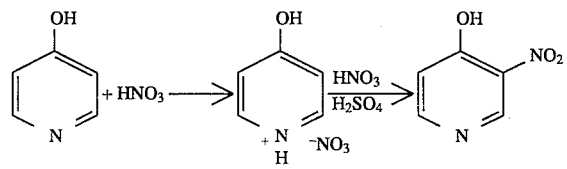

Preparation of 4-hydroxy-3-nitropyridine (starting material).

To a solution of 4-hydroxypyridine (101.8 g, 0.981 mole, 90%) in water (1L) at ice bath temperature was added concentrated nitric acid (182 ml, 4.04 mole). The ice bath was removed and the stirring solution permitted to warm to room temperature then stirred at room temperature for 30 minutes. The solution was then concentrated under reduced pressure by half and refrigerated. The precipitated 4-hydroxypyridinium nitrate was dried in vacuo before it was added to a solution of fuming sulfuric acid (120ml) and fuming nitric acid (156 ml) at ice bath temperatures. This solution was stirred at room temperature overnight (16 hours) then at 85°–95° C. for 5.5 hours, permitted to cool to room temperature then poured over ice (650 g). The resulting precipitate was collected and dried, recrystallized from ethanol/water and dried in vacuo to leave 78.8 g (57.3%) product as pale yellow crystals with melting point 278°–280° C.

Analysis for $C_5H_4N_2O_3$: Calculated C, 42.87; H, 2.88; N, 19.99 Found C, 43.08; H, 2.94; N, 19.97

Part B:

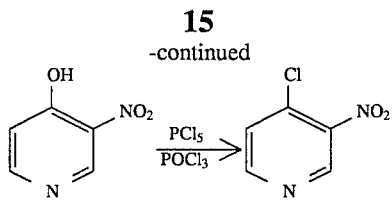

Preparation of 4-chloro-3-nitropyridine.

4-hydroxy-3-nitropyridine (24.6 g, 175 mmole), phosphorus pentachloride (40.0 g, 192 mmole), and phosphorus oxychloride (3.0 ml, 32 mmol) were combined and heated via oil bath. The reaction solution was stirred at oil bath temperatures of 135°–140° C. for 3 hours before the phosphorus oxychloride was distilled off at atmospheric pressure. Relatively low-boiling materials were removed from the reaction vessel via bulb-to-bulb distillation (Aldrich kugelrohr). The material obtained was vacuum distilled (100°–110° C., 3–10 mm) to provide 18.27 g (66%) product as yellow liquid (solidifies in ice bath). NMR. 9.21 ppm (singlet, 1H); 8.80 ppm (doublet, 1H); 7.91 ppm (doublet, 1H).

Part C:

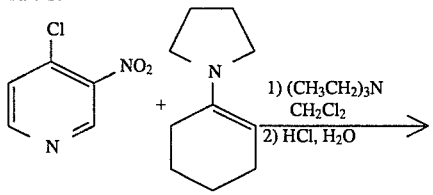

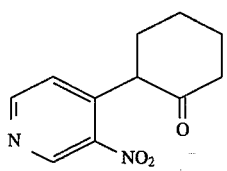

Preparation of 2-(2-nitro-4-pyridyl)cyclohexanone.

To a stirring solution of 4-chloro-3-nitropyridine (9.2 g, ~50 mmole) in $CH_2Cl_2$ (100 ml) under nitrogen were added triethylamine (5.0 ml, 36 mmole) and 1-(1-pyrrolidino)cyclohexene (31 ml, 170 mmole, 90%). The reaction solution was stirred at room temperature for 6 days, then concentrated under reduced pressure and cold in HCl added with stirring until pH=7. The resulting mixture was extracted with ether (2×250 ml) and the combined organic phases washed with brine (40 ml), dried ($MgSO_4$), and concentrated under reduced pressure to 18 g of dark oil. Chromatography ($SiO_2$, step gradient elution from 10% ethyl acetate in hexane to 50% ethyl acetate in hexane) and recrystallization (ether/hexane) provided 5.1 g (46%) of desired product as off-white prisms with melting point 68.5°–70.5° C. Additional purification (chromatography/recrystallization) provided material with melting point 69°–71° C.

Analysis. for $C_{11}H_{12}N_2O_3$: Calculated C, 59.99; H, 5.49; N, 12.72 Found C, 59.69; H, 5.56; N, 12.73

Part D:

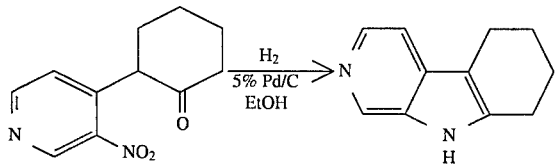

Preparation of 5,6,7,8-tetrahydro-β-carboline.

A mixture of 2-(2-nitro-4-pyridyl)cyclohexanone (2.1 g, 9.5 mmole), 5% palladium on carbon (1.0 g, 0.47 mmole) and ethanol (200 ml, 0.44% toluene) was agitated under 40 psi ($2.76×10^5$ Pa) hydrogen pressure for 3 hours before the reaction mixture was filtered and the filtrate concentrated under reduced pressure. Chromatography of the residue (florisil, step gradient elution from ethyl acetate to 15% methanol in ethyl acetate) followed by recrystallization of the highest $R_f$ band (from ethyl acetate) produced 0.87 g (48%) desired product as beige needles, melting point 200°–201° C.

Analysis. for $C_{11}H_{12}N_2$: Calculated C, 76.71; H, 7.02; N, 16.26 Found C, 76.42; H, 7.02; N, 16.25.

Part E:

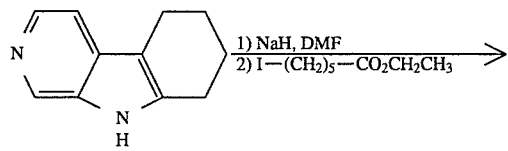

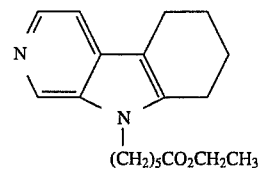

Preparation of ethyl 5,6,7,8-tetrahydro-β-carboline-1-hexanoate.

To a suspension of NaH (0.20 g, 5.0 mmole, 60% dispersion in oil) in anhydrous DMF (5 ml) under nitrogen was added dropwise (over 30 min) a solution of 5,6,7,8-tetrahydro-β-carboline (0.74 g, 4.3 mmole) in anhydrous DMF (15 ml). The reaction mixture was stirred at room temperature until solution was achieved (30 min), whereupon a solution of ethyl 6-iodohexanoate (1.6 g, 5.9 mmole) in anhydrous DMF (4 ml) was added at such a rate that the internal temperature did not exceed 35° C. The reaction solution was then stirred at room temperature under nitrogen for 3.5 hours before it was added to ice water (100 ml) and extracted with ethyl acetate (2×75 ml). The combined organic phases were washed with brine (35 ml), dried ($MgSO_4$), and concentrated in vacuo to a brown oil. Chromatography provided 0.58 g (43%) desired product as yellow oil.

Analysis. for $C_{19}H_{26}N_2O_2$: Calculated C, 72.58; H, 8.33; N, 8.91 Found C, 72.30; H, 8.38; N, 8.92

Part F:

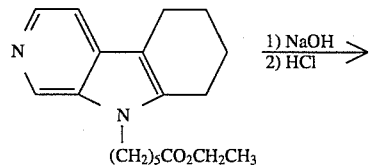

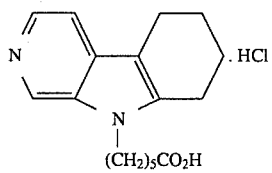

Preparation of 5,6,7,8-tetrahydro-β-carboline-1-hexanoic acid hydrochloride salt.

To a solution of ethyl 5,6,7,8-tetrahydro-β-carboline-1-hexanoate (0.55 g, 1.7 mole) in ethanol (15 ml) was added 5N NaOH (3.0 ml, 15 mole). The reaction solution was stirred at room temperature for 3 hours before it was concentrated under reduced pressure and the residue dissolved in water (5.0 ml). Acidification of this aqueous solution with 5N HCl resulted in the formation of a colorless crystalline precipitate which, after drying, left 0.35 g (64%) desired product with melting point 264°–266° C. (dec.).

Analysis for $C_{17}H_{23}C_1N_2O_2$ Calculated C, 63.25; H, 7.18; N, 8.68 Found C, 62.98; H, 7.22; N, 8.60

ASSAY

The ability of the compound of the present invention to be an effective thromboxane synthase inhibitor was evaluated in the following Thromboxane Synthase Inhibition (TSI) Assay with the results shown in Table 1 below:

TABLE 1

| Compound of Example 1 Part F (μM) | *Serum $TXB_2$ (ng/ml) |
|---|---|
| 0 (vehicle) | 375 ± 85.8 |
| 0.01 | 312 ± 88.1 |
| 0.1 | 170 ± 57.5 |
| 1 | 22.4 ± 4.3 |
| 10 | 5.8 ± 2.2 |

*Mean ± SE, n = 3

Method for Thromboxane synthase Inhibition (TSI) Test

The test compound, 5,6,7,8-tetrahydro-β-carboline-1-hexanoic acid hydrochloride salt, (the compound of Example 1, Part F) was dissolved in dimethylsulfoxide at varying concentrations. The compound solutions and dimethylsulfoxide alone (vehicle) were incubated with fresh whole human blood that had been anticoagulated with 0.38% trisodium citrate, for 30 minutes at 37° C. After 30 minutes, 0.025 ml of 0.5M calcium chloride solution was added to each 1 ml of blood and further incubated for one hour at 37° C. Serum was prepared by centrifugation of the blood at 2000× g for 15 minutes in a Beckman table top centrifuge. Serum $TXB_2$ and 6-keto-$PGF_{1\alpha}$, the stable metabolites of and markers of synthesis of $TXA_2$ and prostacyclin respectively, were measured by radioimmunoassay by commonly used test methods (see, Refs.,1 & 2 below). Results from the radioimmunoassay of $TXB_2$ are shown in Table 1 and indicate the dose-dependent potency of the compound of Example 1, Part F as a thromboxane synthase inhibitor. These data were used to calculate the $IC_{50}$ (concentration of compound required to reduce thromboxane generation to 50% of that obtained with vehicle alone) which for the compound of Example 1, Part F was 81±26 nH (mean ±SE, n=3).

Data determined from the radioimmunoassay of serum 6-keto-$PGF_{1a}$ (reflecting prostacyclin generation) allowed a determination of the specificity of the compound of Example 1, Part F for the inhibition of thromboxane synthase versus cyclooxygenase and prostacyclin synthase as indicated by the serum levels of 6-keto-$PGF_{1\alpha}$. These values decrease in the presence of a non-specific inhibitor (e.g., aspirin) but are unchanged or increased by specific TSI. The data in Table 2 documents the expected dose-dependent stimulatory effect of the compound of Example 1, Part F on human serum 6-keto-$PGF_{1\alpha}$ levels and confirm the specific TSI by the compound of Example 1, Part F.

TABLE 2

| Compound of Example 1 Part F (μM) | Serum 6-keto-$PGF_{1a}$ *(ng/ml) |
|---|---|
| 0 (vehicle) | 1.6 ± 0.2 |
| 0.01 | 1.9 ± 0.1 |
| 0.1 | 2.8 ± 0.1 |
| 1 | 3.2 ± 0.1 |
| 10 | 3.4 ± 0.2 |

*Mean ± SE, n = 3

The oral activity of the compound of Example 1, Part P was established by treating rats via the oral route with solutions of the compound and one hour later collecting blood. The blood was allowed to clot in glass tubes for 1 hour at 37° C. Serum was collected after sedimentation of the clot by centrifugation at 2000× g for 15 minutes in a Beckman table top centrifuge. The levels of $TXB_2$ were measured in the serum by radioimmunoassay. Decreased levels of $TXB_2$ indicate the presence of compound in the blood resulting from oral absorption. The results of these experiments are shown in Table 3 and document the availability of the compound by the oral route of administration and the dose-dependency of the desired inhibitory effect on serum $TXB_2$.

TABLE 3

| Administered Dose of Compound of Example 1 Part F (mg/kg, p.o.) | Serum $TXB_2$ *(ng/ml) |
|---|---|
| 0 | 298 ± 1.7 |
| 1 | 137 ± 12 |
| 10 | 10.7 ± 2.0 |

*Mean ± SE, n = 3

Ref. 1. Sors, H., Pradelles, P and Dray, F. *Prostaglandins*, 16:277, 1978

Ref. 2. Dray, et al. *Advances in Prostaglandin and Thromboxane Research* 6:167, 1980.

What is claimed is:

1. A polyhydronorharman compound which inactivates $TXA_2$ synthase in human blood platelets and other cells, said compound represented by the formula (III):

(III)

wherein;

p is an integer 4 or 5.

2. A compound selected from the group consisting of the following:

(a) ethyl 5,6,7,8-tetrahydro-β-carboline-1-pentanoate, (b) ethyl 5,6,7,8-tetrahydro-β-carboline-1-hexanoate, (c) ethyl 5,6,7,8-tetrahydro-β-carboline-1-heptanoate, and (d) mixtures of any of (a) thru (c);

or a pharmaceutically acceptable salt, solvate and prodrug derivative thereof.

3. A pharmaceutical formulation comprising an effective amount of the compound of claim 1 together with a pharmaceutically acceptable carrier or diluent therefor.

4. A polyhydronorharman compound, or a pharmacologically acceptable salt, solvate, or aliphatic ester prodrug thereof, which compound inactivates $TXA_2$ synthase in mammalian human blood platelets and other cells, and said compound is represented by the formula (II):

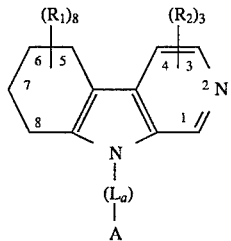

wherein;

$R_1$ is a radical at position 5, 6, 7, and 8 where each $R_1$ is independently selected from hydrogen, hydroxy, halogen, $C_1$–$C_{12}$ alkyl, $C_1$–$C_{12}$ alkoxy, and $C_4$–$C_8$ cycloalkyl, $R_2$ is hydrogen;

$(L_a)$ is a divalent linking group selected from the following formulae:

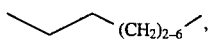

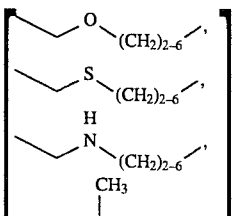

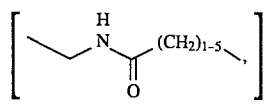

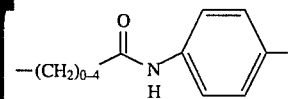

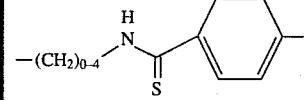

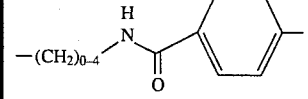

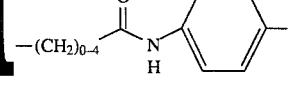

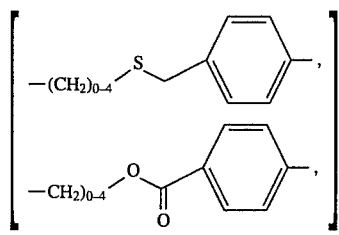

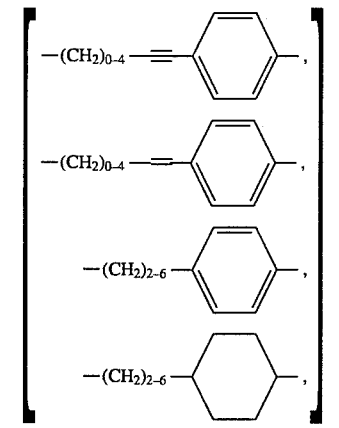

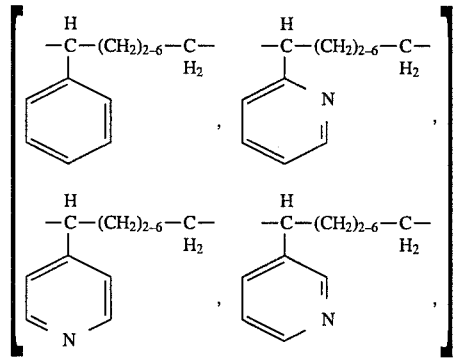

-continued

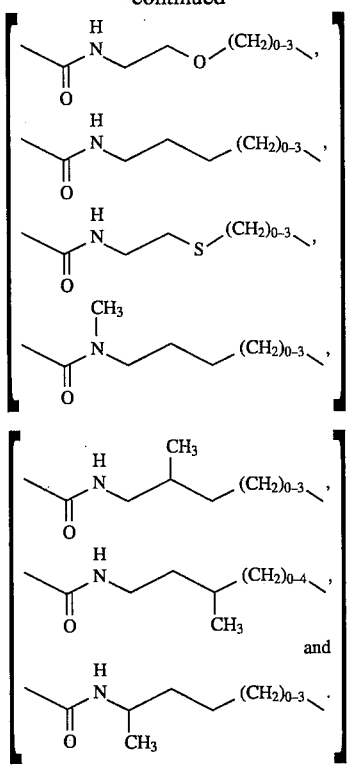

and A is an acidic group selected from the following:

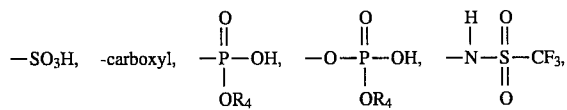

and where $R_4$ is selected from hydrogen, $C_1$–$C_{12}$ alkyl, phenyl or substituted phenyl.

5. A polyhydronorharman compound which inactivates $TXA_2$ synthase in mammalian human blood platelets and other cells, said compound represented by the formula (II):

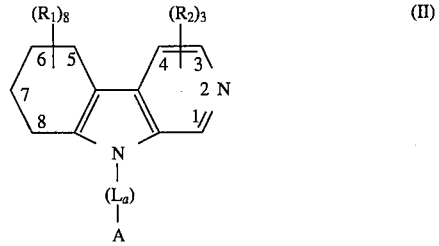

wherein;

$R_1$ and $R_2$ are hydrogen;

$(L_a)$ is a divalent linking group selected from

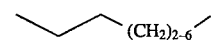

or

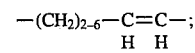

and A is a carboxyl group or a pharmacologically acceptable salt, solvate, or ethyl ester prodrug thereof.

6. A pharmaceutical formulation comprising an effective amount of the compound of claim 5 together with a pharmaceutically acceptable carrier or diluent therefor.

7. A method of inactivating the $TXA_2$ synthase in mammalian blood platelets and other cells by administering to a mammal an effective dose of a polyhydronorharman compound of claim 5.

* * * * *